United States Patent
Yin et al.

(10) Patent No.: US 11,357,480 B2
(45) Date of Patent: Jun. 14, 2022

(54) QUANTITATIVE SHEAR WAVE ELASTICITY IMAGING METHOD AND SYSTEM

(71) Applicant: Saset Chengdu Technology Ltd., Chengdu (CN)

(72) Inventors: Hao Yin, Chengdu (CN); Dan Shi, Chengdu (CN); Xiyao Liu, Seattle, WA (US); Dongquan Liu, Chengdu (CN)

(73) Assignee: Saset Chengdu Technology Ltd., Chengdu (CN)

( * ) Notice: Subject to any disclaimer, the term of this patent is extended or adjusted under 35 U.S.C. 154(b) by 424 days.

(21) Appl. No.: 16/346,079

(22) PCT Filed: Oct. 20, 2017

(86) PCT No.: PCT/CN2017/107120
§ 371 (c)(1),
(2) Date: Apr. 29, 2019

(87) PCT Pub. No.: WO2018/082458
PCT Pub. Date: May 11, 2018

(65) Prior Publication Data
US 2019/0254639 A1  Aug. 22, 2019

(30) Foreign Application Priority Data

Nov. 4, 2016 (CN) .......................... 201610973108.8
Nov. 4, 2016 (CN) .......................... 201610973110.5

(51) Int. Cl.
*A61B 8/00* (2006.01)
*A61B 8/14* (2006.01)
*A61B 8/08* (2006.01)

(52) U.S. Cl.
CPC .................. *A61B 8/54* (2013.01); *A61B 8/08* (2013.01); *A61B 8/085* (2013.01); *A61B 8/14* (2013.01); *A61B 8/485* (2013.01)

(58) Field of Classification Search
None
See application file for complete search history.

(56) References Cited

U.S. PATENT DOCUMENTS 8,225,666 B2    7/2012  McAleavey
2008/0249408 A1*  10/2008  Palmeri .................. A61B 8/485
                                                            600/438
(Continued)

FOREIGN PATENT DOCUMENTS

CN        101869485 A      10/2010
CN        104055541 A       9/2014
(Continued)

OTHER PUBLICATIONS

International Search Report; International Searching Authority/CN dated Jan. 24, 2018; International Application No. PCT/CN2017/107120; 3 pages; International Searching Authority/State Intellectual Property Office of the P.R. China; Beijing, China.

*Primary Examiner* — Katherine L Fernandez
*Assistant Examiner* — Farouk A Bruce
(74) *Attorney, Agent, or Firm* — Andrew D. Fortney; Central California IP Group, P.C.

(57) ABSTRACT

A quantitative shear wave elasticity imaging method and system relates to the technical field of medical ultrasound imaging. The provided ultrasound quantitative elasticity imaging method and system are based on a sliding window linear fitting strain and use a two-dimensional linear fitting shear wave velocity detection algorithm, and thus, the anti-noise capability is stronger, and the result is more reliable. Moreover, where the load of an ultrasonic front-end storage and transmission module is not additionally increased, global ultrasonic quantitative elasticity imaging is realized, thereby significantly reducing the design difficulty of the ultrasound quantitative elasticity imaging system and the device cost.

8 Claims, 4 Drawing Sheets

(56) References Cited

U.S. PATENT DOCUMENTS

| | | | |
|---|---|---|---|
| 2009/0056453 A1 | 3/2009 | McAleavey | |
| 2013/0261452 A1* | 10/2013 | Tamura | A61B 8/485 |
| | | | 600/438 |
| 2014/0088421 A1 | 3/2014 | Guzina et al. | |
| 2014/0276049 A1* | 9/2014 | Doherty | A61B 8/485 |
| | | | 600/438 |
| 2015/0032002 A1* | 1/2015 | Rothberg | A61B 8/4483 |
| | | | 600/440 |
| 2016/0030005 A1* | 2/2016 | Kulakowski, Jr. | A61B 8/4455 |
| | | | 600/438 |

FOREIGN PATENT DOCUMENTS

| | | |
|---|---|---|
| CN | 104605891 A | 5/2015 |
| CN | 106618638 A | 5/2017 |
| CN | 106618639 A | 5/2017 |
| WO | 2008141220 A1 | 11/2008 |

* cited by examiner

QUANTITATIVE SHEAR WAVE ELASTICITY IMAGING METHOD AND SYSTEM

CROSS-REFERENCE TO RELATED APPLICATIONS

This application claims priority to and is a continuation of PCT/CN2017/107120, filed on Oct. 20, 2017, which claims priority to Chinese Patent Application Nos. 201610973108.8, filed on Nov. 4, 2016, and 201610973110.5, filed on Nov. 4, 2016, the entireties of which are hereby incorporated by reference.

TECHNICAL FIELD

The present invention relates to the technical field of medical ultrasound imaging, and in particular, to a quantitative shear wave elasticity imaging method and system.

BACKGROUND ART

Clinically, changes in the mechanical characteristics of human tissues are often the most important early warning signals for tumor diseases. As the tumor grows, the viscoelasticity of the pathological tissue changes significantly compared with the normal tissue. For example, the breast cancer is approximately 90 times different from the surrounding normal tissue. The shear moduli of elasticity of fibrous tissues, non-invasive cancerous tissues and invasive cancerous tissues are also greatly different. Therefore, obtaining parameter information related to viscoelasticity of human tissues (such as deformation displacement and shear wave velocity) is of great significance in the field of medical diagnosis.

Medical ultrasound elasticity imaging is an ultrasound imaging modality of displaying the elasticity modulus or stiffness of a tissue through tissue motion. The conventional freehand elasticity imaging modality requires a doctor to use a probe to compress a detection part to force the movement, thereby obtaining tissue elasticity information. The shortcoming of this modality is that: the doctor needs to compress the detected part with an appropriate operation, and this is quite subjective; because compression by a doctor is needed, it is difficult to directly compare results of operations by different doctors or the results of the operations by a same doctor at different times, and it is difficult to reproduce the detection result, which usually can only be used as a qualitative detection result. It is impossible to obtain quantitative detection information for disease tracking and postoperative observation.

The ultrasound elasticity imaging technology that can perform quantitative analysis at present is mainly based on acoustic radiation force imaging (ARFI). The ARFI uses the focused ultrasonic excitation pulse in the medical ultrasonic power range to generate an acoustic radiation force in the focus region of the bio-viscoelastic tissue, to cause the tissue to deform, and then uses the echo signal of the tracking pulse to detect the deformed displacement of the tissue at different time points through the correlation-based delay calculation method, which is mapped to qualitatively reflect the viscoelastic properties of the tissue. ARFI elasticity imaging overcomes the shortcomings of traditional freehand elasticity imaging that cannot effectively compress deep tissue from outside the body and cause poor repeatability due to different operator habits. However, the shortcoming is that the image displays the relative deformed displacement difference of the tissue, and the elasticity modulus of the tissue cannot be estimated completely quantitatively. Based on ARFI technology-derived ultrasound shear wave imaging (SWI), the shear wave velocity of lateral propagation is estimated according to the displacement-time curves of multiple points in the horizontal direction by adjusting the way of pulse excitation, and then the elasticity modulus of the tissue is finally quantitatively reconstructed to form a two-dimensional image by using the intrinsic relationship between the shear wave propagation characteristics and the elasticity characteristics of the biological tissue.

However, the existing quantitative elasticity imaging SWI requires the use of the original radio frequency signal data before the ultrasound front-end beamforming, and needs to be based on plane wave transmission and reception. The plane wave technology requires N×c/2z calculations per second, where N is the number of parallel received sound beams, c is the speed of sound, and z is the depth of scan. However, the calculation amount of the conventional beamforming method is much smaller, and only one M/Pth, where M is the number of transmissions, P is the parallel number, for example, M is equal to 100, and when P is equal to 2, the calculation amount of the plane wave method is at least 50 times (sometimes even hundreds of times) than that of the conventional ARFI method; in addition to the huge difference in the amount of calculation, the beamforming of the plane wave based receive-end software also needs to store a large number of original echo signals, which significantly increases the data storage and the cost of transmission hardware, and is not convenient for integration with medical ultrasound systems and spread of application.

SUMMARY OF THE INVENTION

The objective of the present invention is to overcome the problem that calculation amount is large, design of required hardware is difficult, and the computation cost is high caused by using original radio frequency signals (without beamforming) in the existing quantitative elasticity imaging technology, and to provide a quantitative ultrasound elasticity imaging method and system with low device requirement and small calculation amount.

To achieve the foregoing inventive objective, the present invention provides the following technical solutions:

A quantitative shear wave elasticity imaging method, including the following steps:

performing ARFI detection, and obtaining a strain $\varepsilon_{ref}$ at a specified position in a focus region;

performing shear wave detection, and obtaining a single-point shear wave velocity $c_{ref}$ at the specified position in the focus region;

calculating a shear wave velocity c at each position according to the single-point shear wave velocity at the specified position; and calculating a shear wave velocity according to the strain at each position and obtaining a quantitative shear wave elasticity image E at each position.

Further, the strain at the specified position in the focus region $$\varepsilon_{ref} = \frac{\sum_{i=1}^{N}(z_i - \bar{z})(y_i - \bar{y})}{\sum_{i=1}^{N}(z_i - \bar{z})^2},$$

where N is window size of gradient sliding calculation, $z_i$ represents a depth coordinate at the specified position, $\bar{z}$ represents an average value of coordinates at positions in the window calculated through gradient sliding, $y_i$ represents a displacement at a current point in the window calculated through gradient sliding, and $\bar{y}$ represents an average value of displacements at positions in the window calculated through gradient sliding.

Further, the single-point shear wave velocity is calculated by a two-dimensional linear fitting method according to a lateral distance and an axial distance of the specified measurement points, as well as a time required by each specified measurement point to reach a maximum lateral displacement.

Further, the single-point shear wave velocity $c_{ref}$ is obtained through a formula $X=A\beta$, wherein $$X = \begin{bmatrix} x_1 \\ x_2 \\ M \\ x_m \end{bmatrix}, A = \begin{bmatrix} 1 & t_1 & z_1 \\ 1 & t_2 & z_2 \\ M & M & M \\ 1 & t_m & z_m \end{bmatrix}, \text{ and } \beta = \begin{bmatrix} \beta_0 \\ \beta_1 \\ \beta_2 \end{bmatrix};$$

in the formula, $x_i$ represents the lateral distance of the specified measurement point, $t_i$ represents the time required by the specified measurement point to reach the maximum displacement, $z_i$ represents the axial distance of the specified measurement point, $\beta_0, \beta_1, \beta_2$ are linear fitting model parameters, a physical meaning of $\beta_1$ is the calculated single-point shear wave velocity $c_{ref}$ at the specified measurement point, and m represents the number of sampling points. $\beta_0$ and $\beta_2$ are regression coefficients calculated in the process of calculating the single-point shear wave velocity $c_{ref}$ by using the foregoing formula, and the two coefficients are not used in this method.

Further, the shear wave velocity at each position $$c = \sqrt{\frac{\varepsilon_{ref}}{\gamma \varepsilon}} c_{ref},$$

in the focus region, a value of $\gamma \varepsilon$ is 1; in an axial region outside the focus region, $\gamma \varepsilon = e^{(z/\sigma)^n}$, wherein z is an axial distance, n and $\sigma$ are system constants of excitation sound field, value ranges of them are both from 0 to 10, and values of the two parameters: n and $\sigma$ may be the same or different.

Further, the focus region $DoF=8(f\#)^2 \lambda$, $\lambda$ represents a wavelength, $f\#$ is an aperture control parameter, and a value range of $f\#$ is real numbers between 0 and 5.

Further, the quantitative shear wave elasticity image $E=3\rho c^2$, and $\rho$ is a medium density in a measured region.

The present invention also provides an ultrasound quantitative elasticity imaging system with low device requirement and small calculation amount, including:

a shear wave pulse generator, configured to transmit a shear wave exciting pulse and a detection pulse signal;

an ARFI wave pulse generator, configured to transmit an ARFI exciting pulse and a sequence of detection pulse signals;

a probe, configured to receive shear wave echo signals and ARFI echo signals;

a control apparatus, configured to: control switches of the shear wave pulse generator and the ARFI wave pulse generator to receive the shear wave echo signals and the ARFI echo signals, and calculate a strain $\varepsilon_{ref}$ at a specified position according to the ARFI echo signal; calculate a single-point shear wave velocity $c_{ref}$ at the specified position according to the shear wave echo signal; calculate a shear wave velocity c at each position according to the single-point shear wave velocity; and obtain a quantitative shear wave elasticity image E at each position; and a display apparatus, configured to display the quantitative shear wave elasticity image E.

Further, the probe includes a beamformer, configured to perform beamforming on the ARFI echo signal or the shear wave echo signal into an echo radio frequency signal.

Further, the control apparatus includes a shear wave signal processing module and a single-point shear wave velocity calculation module;

the shear wave signal processing module receives the shear wave radio frequency echo signal from the probe, and calculates shear wave displacement-time data at specified positions of the measured tissue through demodulation and displacement estimation; and the single-point shear wave velocity calculation module calculates the shear wave velocity $c_{ref}$ at the specified position according to the shear wave displacement-time data, and the shear wave velocity at the specified position is obtained through a formula $X=A\beta$, where $$X = \begin{bmatrix} x_1 \\ x_2 \\ M \\ x_m \end{bmatrix}, A = \begin{bmatrix} 1 & t_1 & z_1 \\ 1 & t_2 & z_2 \\ M & M & M \\ 1 & t_m & z_m \end{bmatrix}, \text{ and } \beta = \begin{bmatrix} \beta_0 \\ \beta_1 \\ \beta_2 \end{bmatrix};$$

in the formula, $x_i$ represents a lateral distance of a specified measurement point, $t_i$ represents a time required by the specified measurement point to reach a maximum displacement, $z_i$ represents an axial distance of the specified measurement point, $\beta_0, \beta_1, \beta_2$ are linear fitting model parameters, a physical meaning of $\beta_1$ is the calculated single-point shear wave velocity $c_{ref}$ at the specified measurement point, and m represents the number of sampling points.

Further, the control apparatus further includes an ARFI signal processing module and a strain calculation module;

the ARFI signal processing module is configured to: receive the ARFI radio frequency echo signal from the probe, and to calculate ARFI displacement-time data at specified positions of the measured tissue through demodulation and displacement estimation; and the strain calculation module calculates the strain $$\varepsilon_{ref} = \frac{\sum_{i=1}^{N}(z_i - \bar{z})(y_i - \bar{y})}{\sum_{i=1}^{N}(z_i - \bar{z})^2}$$

at the specified position according to the ARFI displacement-time data, where N is calculating a size of a window through gradient sliding, $z_i$ represents a depth coordinate at the specified position, $\bar{z}$ represents an average value of coordinates at positions in the window calculated through gradient sliding, $y_i$ represents a displacement at a current point in the window calculated through gradient sliding, and $\bar{y}$ represents an average value of displacements at positions in the window calculated through gradient sliding.

Further, the control apparatus further includes an elasticity modulus calculation module; the control apparatus further includes a wave velocity calculation module and an elasticity modulus calculation module;

the wave velocity calculation module is configured to calculate the shear wave velocity $$c = \sqrt{\frac{\varepsilon_{ref}}{\gamma\varepsilon}} \, c_{ref}$$

at each position according to the single-point shear wave velocity at the specified position, in the focus region, a value of $\gamma\varepsilon$ is 1; in an axial region outside the focus region, $\gamma\varepsilon = e^{(z/\sigma)^n}$, where z is an axial distance, n and $\sigma$ are system constants indicating an excitation sound field, value ranges of them are both 0 to 10, and values of the two parameters: n and $\sigma$ may be the same or different; and the elasticity image calculation module is configured to obtain the quantitative shear wave elasticity image c at each position according to $\varepsilon_{ref}$ and the strain $E=3\rho c^2$, where $\rho$ is a medium density in a measured region.

Further, the control apparatus controls the shear wave pulse generator and the ARFI pulse generator to alternately transmit.

Further, the shear wave pulse generator and the ARFI pulse generator are implemented by a same circuit, and are controlled by the control apparatus to send a shear wave pulse or an ARFI pulse; and the shear wave pulse generator and the ARFI pulse generator are implemented by respective independent circuits, and start-up and switch-off time of them is controlled by the control apparatus.

Further, there are a total of more than 24 paths of shear wave pulse generators and/or ARFI pulse generators.

Further, the shear wave pulse generator or ARFI pulse generator includes a driver amplifier, a pulse generator, an over-current and over-voltage protection circuit, and a Tx/Rx switch that are sequentially connected in series, and a limiting amplifier and a ADC circuit that are fed back by the Tx/Rx switch.

Compared with the Prior Art, the Present Invention has the Following Beneficial Effects:

The ultrasound quantitative elasticity imaging method and system provided in the present invention are based on a sliding window linear fitting strain and use a two-dimensional linear fitting shear wave velocity detection algorithm, and thus, the robustness is better, the anti-noise capability is stronger, and the result is more reliable. Moreover, where the load of an ultrasonic front-end storage and transmission module is not additionally increased, global ultrasonic quantitative elasticity imaging is realized, thereby significantly reducing the design difficulty of the ultrasound quantitative elasticity imaging system and the device cost. An effective circuit switching and protection module is disposed in the present invention, so that when satisfying different transmission sequence requirements of the ARFI and shear wave, the system effectively protects the human body and the system circuit, and performs sound excitation to the greatest extent to achieve a better detection effect.

DETAILED DESCRIPTION OF THE INVENTION

The present invention is further described in detail below with reference to the accompanying drawings and specific embodiments. However, this should not be understood as that the scope of the subject matter of the present invention is limited only to the following embodiments. Any technology implemented based on content of the present invention falls within the scope of the present invention.

Figure 1:
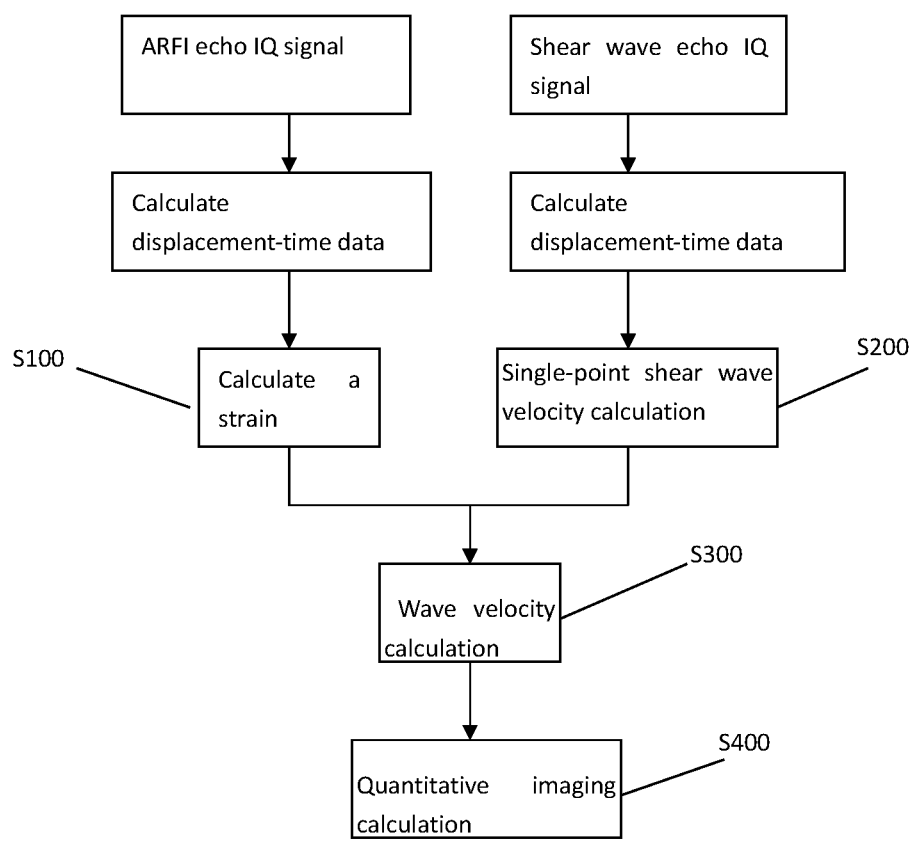
FIG. 1 is a flowchart of an ultrasound quantitative elasticity imaging method according to the present invention.
Figure 2:
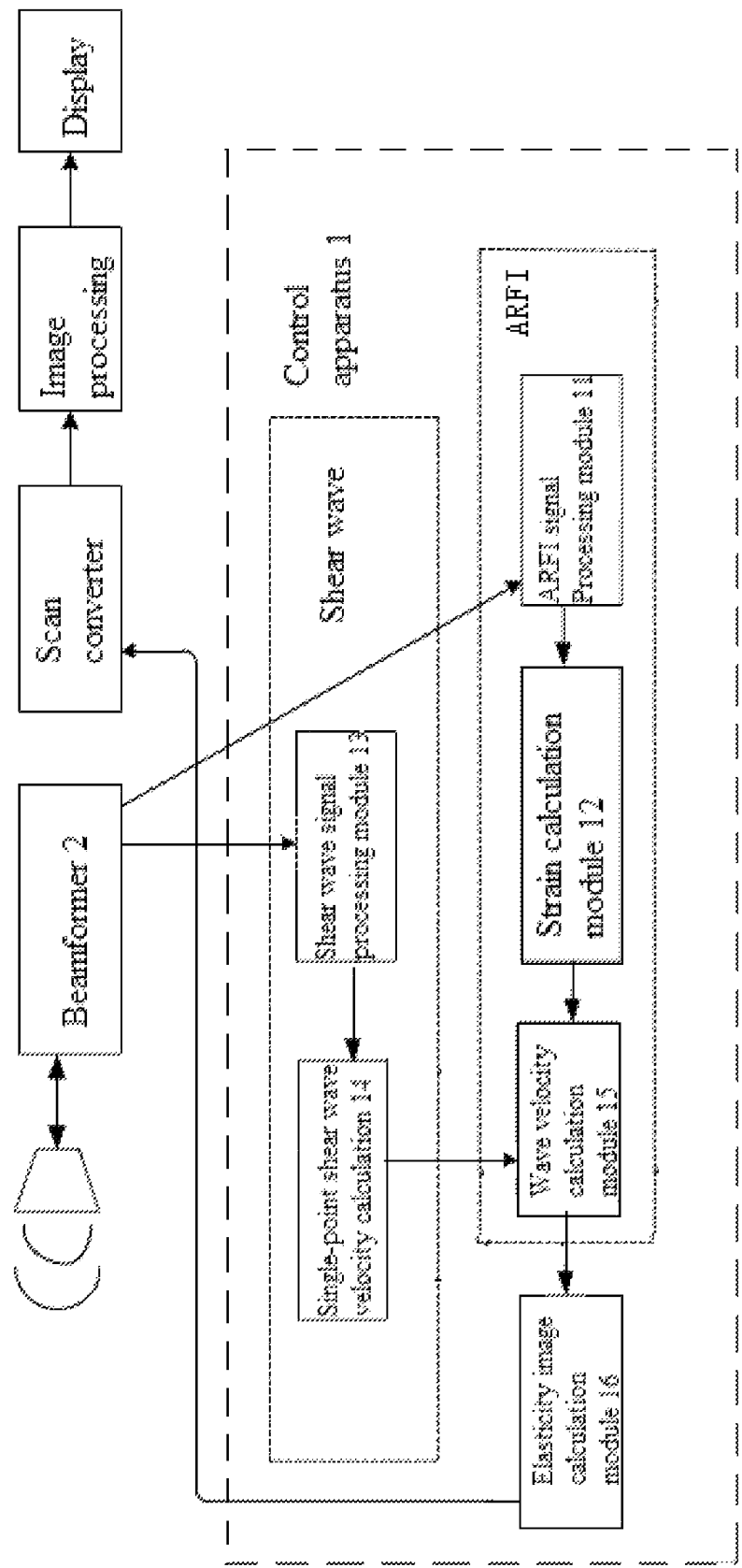
FIG. 2 is a block diagram of an ultrasound quantitative elasticity imaging system according to the present invention.

Embodiment 1: as shown in FIG. 1, the present invention provides a quantitative shear wave elasticity imaging method, including the following steps:

S100: Perform ARFI detection, and obtain a strain $\varepsilon_{ref}$ at a specified position in a focus region.

S200: Perform shear wave detection, and obtain a single-point shear wave velocity $c_{ref}$ at the specified position in the focus region.

There is no special requirement for the execution sequence of steps S100 and S200. For example, S100 may be executed first, then S200 may be executed, or S200 may be executed first, and then S100 is executed. The example in FIG. 1 uses an orthogonal demodulation (IQ) echo signal, or one or more of an IQ echo signal, a channel echo radio frequency (RF) signal, and a beamformed radio frequency (RF) signal may be detected.

S300: Calculate a shear wave velocity c at each position according to the single-point shear wave velocity.

S400: Calculate a shear wave velocity according to the strain at each position and obtain a quantitative shear wave elasticity image E at each position.

Specifically, the strain at the specified position in the focus region $$\varepsilon_{ref} = \frac{\sum_{i=1}^{N}(z_i - \bar{z})(y_i - \bar{y})}{\sum_{i=1}^{N}(z_i - \bar{z})^2},$$

where N is calculating a size of a window through gradient sliding, $z_i$ represents a depth coordinate at the specified position, $\bar{z}$ represents an average value of coordinates at positions in the window calculated through gradient sliding, $y_i$ represents a displacement at a current point in the window calculated through gradient sliding, and $\bar{y}$ represents an average value of displacements at positions in the window calculated through gradient sliding.

The single-point shear wave velocity is calculated by using a two-dimensional linear fitting method according to a lateral distance and an axial distance of a specified measurement point and a time required by each specified measurement point to reach a maximum lateral displacement.

The single-point shear wave velocity $c_{ref}$ is obtained through a formula $X=A\beta$, where $$X = \begin{bmatrix} x_1 \\ x_2 \\ M \\ x_m \end{bmatrix}, A = \begin{bmatrix} 1 & t_1 & z_1 \\ 1 & t_2 & z_2 \\ M & M & M \\ 1 & t_m & z_m \end{bmatrix}, \text{ and } \beta = \begin{bmatrix} \beta_0 \\ \beta_1 \\ \beta_2 \end{bmatrix};$$

in the formula, I depths are usually preset in an axial depth, and J specified positions (points) are preset in each depth, and there are a total of m specified positions (points), m=I*J; the time required by each position (point) to reach a maximum displacement under the effect of the shear wave is considered as the time required by the shear wave to propagate to the position (point); the time required by the shear wave to transmit to the position (point) can be obtained through shear wave displacement-time data, namely, $t_i$. In addition, $z_i$ represents the axial distance (characterizing a depth position) of the specified measurement position (point) in the axial depth, $x_i$ represents the lateral distance (characterizing a lateral position) of the specified measurement position (point). To be specific, when each specified position (point) is selected, various element values in X and a value of $z_i$ have been determined, and calculation can be completed provided that the time $t_i$ required by each specified position (point) to achieve the maximum displacement is found from the shear wave displacement-time data; in the formula, $\beta_1$ is the calculated single-point shear wave velocity $c_{ref}$ at the specified measurement point, and it should also be noted that $\beta_0$ and $\beta_2$ are regression coefficients calculated in the process of calculating the single-point shear wave velocity $c_{ref}$ by using the foregoing formula, and the two coefficients are not used in this method, and the functions and meanings thereof have no substantive meaning for the present invention.

The shear wave velocity at each position $$c = \sqrt{\frac{\varepsilon_{ref}}{\gamma \varepsilon}} \, c_{ref},$$

in the focus region, a value of $\gamma\varepsilon$ is 1; in an axial region outside the focus region, $\gamma\varepsilon = e^{(z/\sigma)^n}$, wherein z is an axial distance, n and σ are system constants indicating an excitation sound field, value ranges of them are both 0 to 10, and values of the two parameters: n and σ may be the same or different.

The quantitative shear wave elasticity image $E = 3\rho c^2$, and ρ is a medium density in a measured region.

The present invention also provides an ultrasound quantitative elasticity imaging system with a low requirement on a device and a small calculation amount, including:

a shear wave pulse generator, configured to transmit a shear wave exciting pulse and a detection pulse signal;

an ARFI wave pulse generator, configured to transmit an ARFI exciting pulse and a detection pulse signal;

a probe, configured to receive a shear wave echo signal and an ARFI echo signal;

a control apparatus 1, configured to: control switches of the shear wave pulse generator and the ARFI wave pulse generator to receive the shear wave echo signal and the ARFI echo signal, and calculate a strain $\varepsilon_{ref}$ at a specified position according to the ARFI echo signal; calculate a single-point shear wave velocity $c_{ref}$ at the specified position according to the shear wave echo signal; calculate a shear wave velocity c at each position according to the single-point shear wave velocity; and obtain a quantitative shear wave elasticity image E at each position; and a display apparatus, configured to display the quantitative shear wave elasticity image E. Specifically, before display, a series of processing processes such as scan conversion and smoothing processing performed on the data of the elasticity image E calculated by the control apparatus are further included, and finally, the image is presented to a user by using a display.

The probe includes a beamformer 2, configured to perform beamforming on the ARFI echo signal or the shear wave echo signal into an echo radio frequency signal.

The control apparatus 1 includes a shear wave signal processing module 13 and a single-point shear wave velocity calculation module 14;

the shear wave signal processing module 13 receives the shear wave echo radio frequency signal from the probe, and demodulates the signal into IQ data, and further performs displacement on the IQ data to estimate shear wave displacement-time data at a specified position of a measured tissue; and the single-point shear wave velocity calculation module 14 calculates the shear wave velocity $c_{ref}$ at the specified position according to the shear wave displacement-time data, and the shear wave velocity at the specified position is obtained through a formula X=Aβ, where $$X = \begin{bmatrix} x_1 \\ x_2 \\ M \\ x_m \end{bmatrix}, A = \begin{bmatrix} 1 & t_1 & z_1 \\ 1 & t_2 & z_2 \\ M & M & M \\ 1 & t_m & z_m \end{bmatrix}, \text{ and } \beta = \begin{bmatrix} \beta_0 \\ \beta_1 \\ \beta_2 \end{bmatrix};$$

in the formula, $x_i$ represents a lateral distance of a specified measurement point, $t_i$ represents a time required by the specified measurement point to reach a maximum displacement, $z_i$ represents an axial distance of the specified measurement point, $\beta_0, \beta_1, \beta_2$ are linear fitting model parameters, a physical meaning of $\beta_1$ is the calculated single-point shear wave velocity $c_{ref}$ at the specified measurement point, and m represents the number of sampling points.

The control apparatus 1 further includes an ARFI signal processing module 11 and a strain calculation module 12;

the ARFI signal processing module 11 is configured to receive the ARFI echo radio frequency signal from the probe, and demodulate the signal into IQ data, and further perform displacement on the IQ data to estimate ARFI displacement-time data at a specified position of a measured tissue; and the strain calculation module 12 calculates the strain $$\varepsilon_{ref} = \frac{\sum_{i=1}^{N}(z_i - \bar{z})(y_i - \bar{y})}{\sum_{i=1}^{N}(z_i - \bar{z})^2},$$

at the specified position according to the ARFI displacement-time data, where N is calculating a size of a window through gradient sliding, $z_i$ represents a depth coordinate at the specified position, $\bar{z}$ represents an average value of coordinates at positions in the window calculated through gradient sliding, $y_i$ represents a displacement at a current point in the window calculated through gradient sliding, and $\bar{y}$ represents an average value of displacements at positions in the window calculated through gradient sliding.

The control apparatus 1 further includes a wave velocity calculation module 15 and an elasticity modulus calculation module 16;

the wave velocity calculation module 15 is configured to calculate the shear wave velocity $$c = \sqrt{\frac{\varepsilon_{ref}}{\gamma\varepsilon}}\, c_{ref}$$

at each position according to the single-point shear wave velocity at the specified position, in the focus region, a value of $\gamma\varepsilon$ is 1; in an axial region outside the focus region, $\gamma\varepsilon = e^{(z/\sigma)^n}$, where z is an axial distance, n and $\sigma$ are system constants indicating an excitation sound field, value ranges of them are both 0 to 10, and values of the two parameters: n and $\sigma$ may be the same or different; and the elasticity image calculation module 16 is configured to obtain the quantitative shear wave elasticity image $E = 3\rho c^2$ at each position according to c, strains and $\varepsilon_{ref}$, where $\rho$ is a medium density in a measured region.

The control apparatus 1 controls the shear wave pulse generator and the ARFI pulse generator to alternately transmit.

Figure 3:
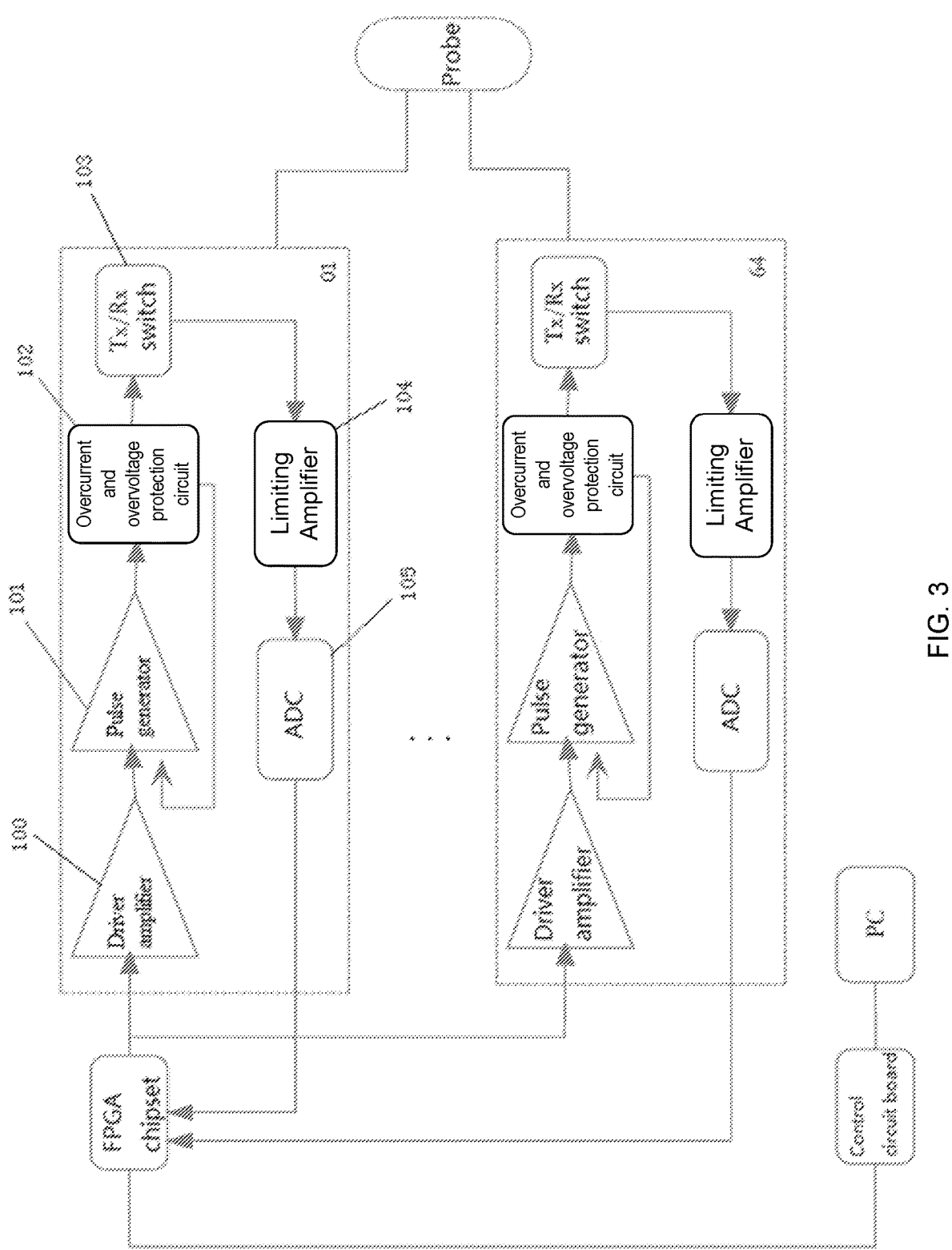
FIG. 3 is a structural block diagram of an example formed by a shear wave pulse generator and/or the ARFI pulse generator in the present invention.

Specifically, as shown in FIG. 3, in some embodiments, a hardware part of the control apparatus 1 may be composed of a PC, a control circuit board, and an FPGA chipset. In other embodiments, the control apparatus may also be composed of integrated circuits completely integrated together. The shear wave signal processing module, the single-point shear wave velocity calculation module, the ARFI signal processing module, the strain calculation module, and the elasticity modulus calculation module are distributed in the foregoing hardware apparatus according to functions.

The shear wave pulse generator and the ARFI pulse generator are implemented by a same circuit, and are controlled by the control apparatus to send a shear wave pulse or an ARFI pulse; or, the shear wave pulse generator and the ARFI pulse generator are implemented by respective independent circuits, and start-up and switch-off time of them is controlled by the control apparatus.

Specifically, in an embodiment in which the shear wave pulse generator and the ARFI pulse generator are implemented by a same circuit, as shown in FIG. 3, the generator includes a driver amplifier 100, a pulse generator 101, an over-current and over-voltage protection circuit 102, and a Tx/Rx switch 103 that are sequentially connected in series, and a limiting amplifier 104 and a ADC 105 that are fed back by the Tx/Rx switch. The over-current and over-voltage protection circuit 102 can enable the system to effectively protect the human body and the system circuit when the system satisfies different transmission sequence requirements of the ARFI and shear wave, and to perform sound excitation to the greatest extent to achieve a better detection effect.

There are a total of more than 24 paths, for example, 48 paths, 64 paths, 128 paths, and 256 paths, of shear wave pulse generators and/or ARFI pulse generators.

In use, the control apparatus controls the pulse generator (the shear wave pulse generator and/or the ARFI pulse generator) to generate excitation and detection pulse signals according to parameter information such as a voltage, a pulse length and a phase set by the user. An ultrasonic wave generated by a transmitting circuit enters a biological tissue under control of a T/R switch, and a receiving circuit receives an echo signal. When transmitting or receiving a signal, the system sets the aperture control parameter f # and the depth of focus z, and uses the formula $$D = \frac{z}{f\#}$$

to control the number of active array elements (pulse generators). In the formula, D is the probe aperture size. That is, the user sets the aperture control parameter f # and the depth of focus z to control the size of the active probe aperture to control the number of active array elements. The user can select the number of active array elements actually required in the maximum number of active array elements (such as 64 paths) according to the situation. For example, if the system includes 64 paths of pulse generators, the maximum probe aperture size that the system can achieve is the area where 64 array elements are distributed. The aperture control parameter f # is usually a real number greater than 0 and less than or equal to 5. Because a force that excites the tissue to generate a deformation is formed in the focus region by the probe by transmitting a short-duration pulse wave according to an option set by the user, and is not related to an operation method of an operator, it can be considered that the force in the effective imaging region is even and uniform. The depth of focus may be described as $DoF = 8(f\#)^2 \lambda$, $\lambda$ representing the wavelength; for example, for a 5 MHz excitation pulse, if the aperture control parameter f # is equal to 2, the speed of sound in the biological tissue is approximately equal to 1540 m/s, then the value of the DoF is approximately 1 cm; when f #=5, the corresponding DoF is 2.5 cm. ARFI elasticity imaging is performed in a line-by-line scan manner. At each horizontal position, an excitation pulse is transmitted according to a same system parameter, to cause a slight deformation of the tissue. Therefore, it can be considered that an acoustic radiation force within a range of 1 cm near the focus can be considered as even and uniform. This region is referred to as the focus region. As mentioned above, in the focus region, the value of $\gamma\varepsilon$ in the shear wave velocity calculation formula $$c = \sqrt{\frac{\varepsilon_{ref}}{\gamma\varepsilon}}\, c_{ref}$$

is 1.

Figure 4:
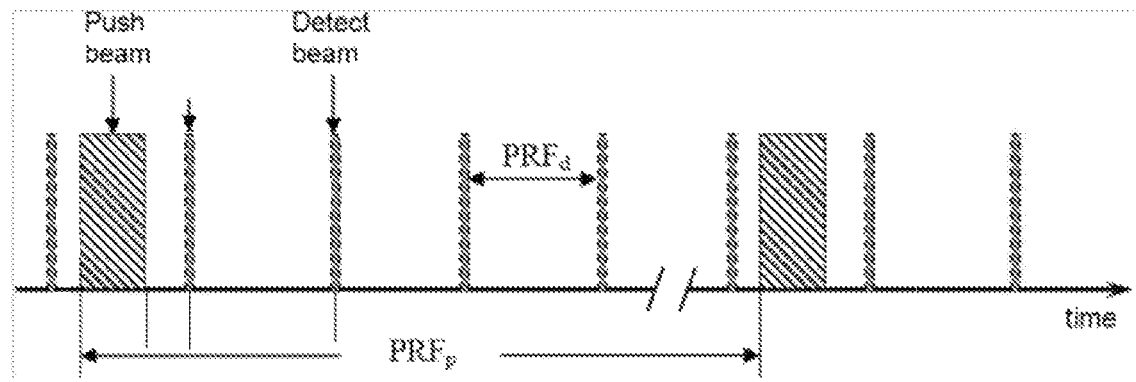
FIG. 4 is a schematic diagram of a transmission pulse sequence used in sound excitation in the present invention.

The transmission pulse sequence is schematically shown in FIG. 4, and the transmission pulse sequence is controlled according to parameters such as the ROI (Region of Interest) window depth position, signal center frequency magnitude, PRF (pulse repeat frequency), excitation voltage, and pulse length. The head of the sequence is one or more detection pulses (detect beams, higher voltages (for example, 80 V, usually the same as B mode), short pulses (for example, 2 cycles)) used as reference signals for tissue displacement information; and next, a plurality of groups of excitation/detection pulse pairs, excitation pulses (push beams, lower voltages (for example, 20 V to 40 V), long pulses (100 to 250 cycles)) used for excitation in a local region near the focus in the tissue to generate micro displacement.

The detection pulse (a short pulse of a high voltage) is used to track the deformation of the tissue during the loading process of the acoustic radiation force load, followed by a series of detection pulses to track the deformation of the tissue after the acoustic radiation force load disappears. The function of the excitation pulse is to enable the local tissue at the focus position to vibrate under safe conditions. The long echo signal cannot be used for displacement estimation due to a poor spatial resolution thereof, and therefore the probe array element turns off the signal apodization when the excitation pulse is transmitted. The amplitudes of transmit signals of all active elements are the same, thereby enhancing energy carried by the signals to generate greater acoustic radiation forces under safe conditions. The long pulse wave frequency used for excitation and the short pulse wave center frequency used for detection may be selected to be the same or different, and the preferred solution is that the center frequencies are different, so that the excitation pulse can be prevented from interfering with the detection pulse echo signal, and moreover, it is easy to distinguish between the excitation and detection echo signals during signal processing.

In addition, the number of long pulse waves in the transmission pulse sequence is variable, and the number of waves in the entire sequence is also variable. Herein, the number of waves that excite the entire sequence at one time is defined as the ensemble size, for example, 16, 24, or 32. The number of long pulse waves (excitation waves)+the number of short pulse waves (reference and detection waves)=the number of sampling volumes, and the size of the gradient sliding calculation window N is any value between 0 and the ensemble size, and is specifically automatically selected by using an adaptive algorithm, and details are not described herein again.

Figure 5:
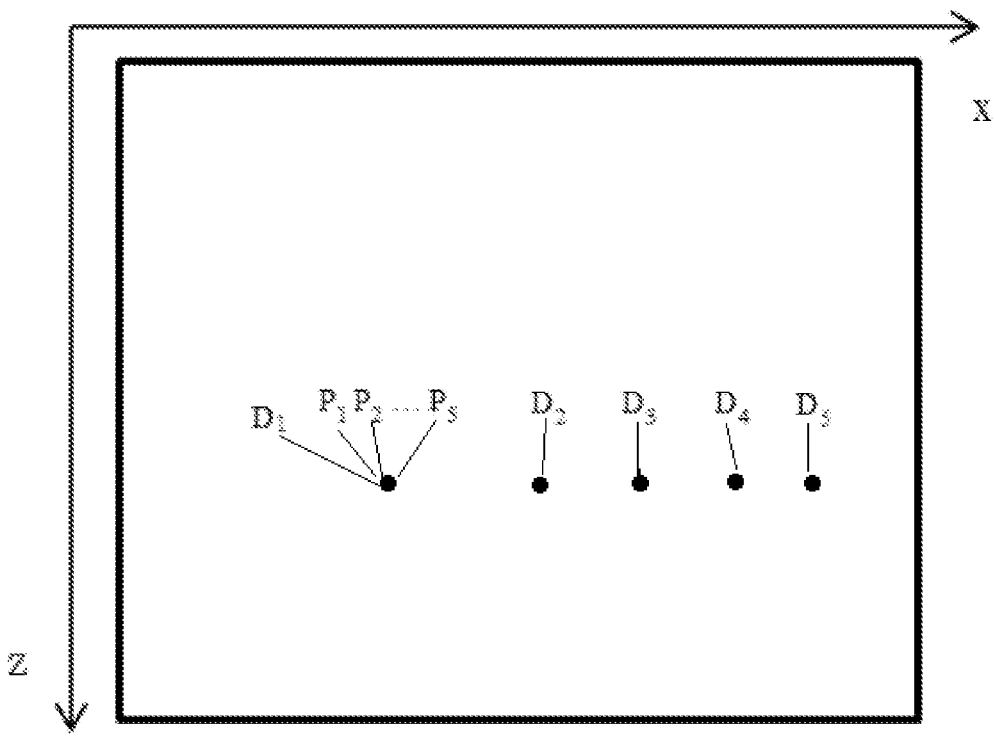
FIG. 5 is a schematic diagram of a pulse transmission manner used in shear wave velocity calculation.

A group of shear wave transmission pulses includes a plurality of transmission pulse sequences at a plurality of different spatial positions, as shown in FIG. 4, where the excitation pulse has a fixed spatial position, and detection pulses of different transmission sequences have different spatial positions. As shown in FIG. 5, D is a detection wave, and P is an excitation wave. If there is a group of shear wave transmission pulses using five transmission pulse sequences with an interval of 1 mm, excitation waves P1, P2, P3, P4 and P5 of the five sequences are all at a same spatial position, and detection waves D1, D2, D3, D4, D5 in the five transmission pulse sequences are at the same or different spatial positions, and moreover, the spatial position of the at least one detection pulse is the same as the position of the excitation pulse, such as D1 in the figure.

The ARFI pulse generator uses the same transmit pulse sequence as the shear wave pulse generator, but the excitation wave remains in the same spatial position as the detected wave during one frame of ARFI imaging scanning.

The invention claimed is:
1. A quantitative shear wave elasticity imaging system, comprising:
 a shear wave pulse generator, configured to transmit a shear wave exciting pulse and a detection pulse signal;
 an Acoustic Radiation Force Imaging (ARFI) wave pulse generator, configured to transmit an ARFI exciting pulse and a detection pulse signal;
 a probe, configured to receive a shear wave echo signal and an ARFI echo signal and comprising a beamformer, configured to perform beamforming on the ARFI echo signal or the shear wave echo signal into a radio frequency echo signal;
 a control apparatus, comprising an ARFI signal processing module and a strain calculation module, wherein:
 the control apparatus is configured to control switches of the shear wave pulse generator and the ARFI wave pulse generator to receive the shear wave echo signal and the ARFI echo signal, and calculate a strain ref at a specified position of a measured tissue according to the ARFI echo signal;
 calculate a single-point shear wave velocity $c_{ref}$ at the specified position according to the shear wave echo signal; calculate a shear wave velocity c at each position according to the single-point shear wave velocity; and obtain a quantitative shear wave elasticity image E at each position,
 the ARFI signal processing module is configured to: receive the radio frequency echo signal from the probe, and estimate ARFI displacement-time data at the specified position of the measured tissue through a demodulation and displacement estimation; and
 the strain calculation module calculates the strain

$$\varepsilon_{ref} = \frac{\sum_{i=1}^{N}(z_i - \bar{z})(y_i - \bar{y})}{\sum_{i=1}^{N}(z_i - \bar{z})^2}$$

at the specified position according to the ARFI displacement-time data, wherein N is calculating a size of a gradient sliding window, $z_i$ represents a depth coordinate at the specified position, $\bar{z}$ represents an average value of coordinates at positions in the gradient sliding window, $y_i$ represents a displacement at a current point in the gradient sliding window, and $\bar{y}$ represents an average value of displacements at positions in the gradient sliding window; and
 a display apparatus, configured to display the quantitative shear wave elasticity image E.
2. The system according to claim 1, wherein the control apparatus comprises a shear wave signal processing module and a single-point shear wave velocity calculation module;
 the shear wave signal processing module receives the radio frequency echo signal from the probe, and estimates shear wave displacement-time data at the specified position of the measured tissue through demodulation and displacement; and
 the single-point shear wave velocity calculation module calculates the shear wave velocity $c_{ref}$ at the specified position according to the shear wave displacement-time data, and the shear wave velocity at the specified position is obtained through a formula $X=A\beta$, wherein $$X = \begin{bmatrix} x_1 \\ x_2 \\ M \\ x_m \end{bmatrix}, A = \begin{bmatrix} 1 & t_1 & z_1 \\ 1 & t_2 & z_2 \\ M & M & M \\ 1 & t_m & z_m \end{bmatrix}, \text{ and } \beta = \begin{bmatrix} \beta_0 \\ \beta_1 \\ \beta_2 \end{bmatrix};$$

in the formula, $x_i$ represents a lateral distance of a specified measurement point, $t_i$ represents a time required by the specified measurement point to reach a maximum displacement, $z_i$ represents an axial distance of the specified measurement point, $\beta_0 \beta_1 \beta_2$ are linear fitting model parameters, a physical meaning of $\beta_1$ is the calculated single-point shear wave velocity $c_{ref}$ at the specified measurement point, and m represents the number of sampling points.

3. The system according to claim 1, wherein the control apparatus further comprises a wave velocity calculation module and an elasticity modulus calculation module;

the wave velocity calculation module is configured to calculate the shear wave velocity according to a formula $$c = \sqrt{\frac{\varepsilon_{ref}}{\gamma \varepsilon}} c_{ref},$$

at each position according to the single-point shear wave velocity at the specified position, and in the focus region, a value of $\gamma\varepsilon$ is 1; in an axial region outside the focus region, $\gamma\varepsilon = e^{(z/o)^n}$, z is an axial distance, n and $\sigma$ are system constants indicating an excitation sound field, value ranges of n and $\sigma$ are 0 to 10, and values of the two parameters n and $\sigma$ may be the same or different; and the elasticity image calculation module is configured to obtain the quantitative shear wave elasticity image $E=3\rho c^2$ at each position according to c, strains, and $\varepsilon_{ref}$, wherein $\rho$ is a medium density in a measured region.

4. The system according to claim 1, characterized in that the control apparatus controls the shear wave pulse generator and the ARFI pulse generator to alternately transmit.

5. The system according to claim 1, wherein the shear wave pulse generator and the ARFI pulse generator are implemented by a same circuit, and are controlled by the control apparatus to send a shear wave pulse or an ARFI pulse.

6. The system according to claim 1, characterized in that there are a total of more than 24 paths of shear wave pulse generators and/or ARFI pulse generators.

7. The system according to claim 1, characterized in that the shear wave pulse generator or the ARFI pulse generator comprises a driver amplifier, a pulse generator, an over-current and over-voltage protection circuit, and a Tx/Rx switch that are sequentially connected in series, and a limiting amplifier and an analog-to-digital converter (ADC) that are fed back by the Tx/Rx switch.

8. The system according to claim 1, wherein the shear wave pulse generator and the ARFI pulse generator are implemented by respective independent circuits, and their respective start-up and switch-off times are controlled by the control apparatus.

* * * * *